United States Patent [19]
Abele et al.

[11] Patent Number: 5,704,913
[45] Date of Patent: Jan. 6, 1998

[54] DILATION CATHETER AND METHOD OF TREATMENT THEREWITH

[75] Inventors: John E. Abele, Concord; Peter M. Nicholas, So. Dartmouth; James C. Wang, Norton, all of Mass.

[73] Assignee: Boston Scientific Corporation, Natick, Mass.

[21] Appl. No.: 246,485

[22] Filed: May 19, 1994

Related U.S. Application Data

[63] Continuation-in-part of Ser. No. 82,594, Jun. 25, 1993, abandoned, which is a continuation-in-part of Ser. No. 17,763, Feb. 16, 1993, abandoned.

[51] Int. Cl.⁶ .............................................. A61M 29/00
[52] U.S. Cl. .......................... 604/101; 604/100; 606/194
[58] Field of Search ........................... 604/96, 101, 49, 604/52, 53, 100; 606/192, 194

[56] References Cited

U.S. PATENT DOCUMENTS

| | | | |
|---|---|---|---|
| 3,720,199 | 3/1973 | Rishton et al. | 128/1 D |
| 4,141,364 | 2/1979 | Schultze | 604/96 |
| 4,233,983 | 11/1980 | Rocco | 128/349 B |
| 4,423,725 | 1/1984 | Baran et al. | 128/207.15 |
| 4,744,366 | 5/1988 | Jang | 128/344 |
| 4,763,654 | 8/1988 | Jang | 128/344 |
| 4,896,669 | 1/1990 | Bhate et al. | 604/96 |
| 4,902,273 | 2/1990 | Choy et al. | 600/18 |
| 5,021,046 | 6/1991 | Wallace | 604/97 |
| 5,078,685 | 1/1992 | Colliver | 604/96 |
| 5,084,060 | 1/1992 | Freund et al. | 606/192 |
| 5,254,089 | 10/1993 | Wang | 606/194 |
| 5,308,323 | 5/1994 | Sogawa et al. | 604/95 |

FOREIGN PATENT DOCUMENTS

| | | |
|---|---|---|
| 1069826 | 1/1984 | U.S.S.R. |
| 89/11889 | 12/1989 | WIPO |

*Primary Examiner*—Corrine M. McDermott
*Attorney, Agent, or Firm*—Frances P. Craig

[57] ABSTRACT

A catheter for insertion into a bodily conduit, especially an artery. The catheter comprises a shaft (26) having at least one lumen (24) for delivery of a fluid inflation media and a double balloon (12) including an array (20) of a plurality of inflatable secondary chambers (22) radially disposed in a cylindrical array around an inflatable primary chamber (16). Each of the secondary chambers (22) shares a common wall (38) with adjacent secondary chambers (22) and a common wall (14) with the primary chamber (16). The secondary chambers (22) are inflated by an array of channels (32) which are separated from each other by webs (40). One or more of the secondary chambers (22) may be in communication with a pressure transducer for measurement of the resistance of, e.g., a stenosis to dilation by the balloon (12). Alternately, a triple balloon (60) has inner secondary chambers (22a) and outer secondary chambers (22b). Also alternately, one or more of the secondary chambers (22) may be adapted to dispense medication. A method for treating a constricted bodily conduit using the catheter is also disclosed.

28 Claims, 7 Drawing Sheets

DILATION CATHETER AND METHOD OF TREATMENT THEREWITH

CROSS REFERENCE TO RELATED APPLICATIONS

This is a continuation-in-part application Ser. No. 08/082,594 filed on Jun. 25, 1993 now abandoned, which is a continuation-in-part of commonly assigned, U.S. patent application Ser. No. 08/017,763, now abandoned filed Feb. 16, 1993, by J. Wang. This application is also related to commonly assigned, U.S. patent application Ser. No. 07/862,415, filed Apr. 2, 1992 by J. Wang, now issued as U.S. Pat. No. 5,254,089. U.S. patent applications Ser. Nos. 08/017,763 and 07/862,415 are hereby incorporated herein by reference.

BACKGROUND OF THE INVENTION

The present invention relates to catheters that can be placed in bodily conduits. The invention particularly relates to coronary dilation catheters for use in administering treatments to widen constricted blood flow passages typically caused by stenoses in, for example, heart valves or coronary arteries, and to methods for administering such treatments using the catheter of the invention.

A stenosis is a region of a blood vessel which has been narrowed to such a degree that blood flow is restricted. If the stenosis is severe, treatment is required to restore adequate blood flow, and often such treatment requires surgery or angioplasty. Coronary angioplasty includes the insertion of a balloon catheter through a patient's artery to the arterial stenosis, and injecting a suitable fluid into the balloon to inflate it. The inflation expands the stenosis radially outwardly and compresses it against the artery wall to increase the cross-sectional area of the artery so that the artery has an acceptable blood flow rate. Angioplasty has become a successful alternative to coronary arterial bypass surgery.

Ordinary balloon catheters have a balloon fastened around the exterior of a hollow catheter tube. A tubular shaft is fastened to the balloon, and the balloon is in fluid flow relation with the interior of the shaft. The shaft provides a fluid supply for inflating the balloon.

To assure optimal results in a balloon angioplasty procedure, the diameter of the balloon must be carefully matched to the diameter of the (unobstructed) artery. A too small balloon may not sufficiently dilate the arterial lumen, while a too large balloon may lead to damage to the artery wall. Occasionally during the dilation procedure, a balloon catheter must be withdrawn and another catheter with a smaller or larger balloon inserted. This substitution lengthens the procedure and can increase the risk to the patient.

To address this problem, catheters have been devised using balloons of a compliant, e.g. elastomeric, material capable of inflation to a range of diameters. These compliant balloons, however, may be subject to over-dilation with its potential for artery wall damage.

Another approach to solving the problem utilizes multiple balloons of different diameters mounted sequentially on a multiple-lumen catheter shaft. Each balloon is individually inflatable and deflatable using a separate lumen. This approach, however, presents several drawbacks. For example, when using the proximal balloon, the distal balloon must be inserted further downstream in the artery; in some instances there may not be sufficient room downstream to accomplish this. Also, when two consecutive balloons are disposed on a single catheter, the catheter is more difficult to maneuver into position to treat the stenosis.

Coaxial, concentric, double balloons have also been designed, with a smaller balloon inside a larger, separate balloon, each balloon inflated by a separate lumen. This approach, however, can complicate the so-called "piecing back" of balloons which have burst during the dilation procedure. Even the strongest balloons will occasionally fail during dilation, for example bursting during inflation within the artery being treated. When a balloon has burst, it must be withdrawn and an attempt must be made to fit the balloon pieces together ("piecing back") to ensure that no balloon fractions have been left behind. With the prior art double balloon design, the piecing-back process becomes very difficult and complicated because two separate balloons are involved. Also, the deflated double balloons can be bulky, complicating withdrawal.

SUMMARY OF THE INVENTION

In a first aspect, the invention is a catheter for insertion into a bodily conduit. The catheter includes a shaft, a primary balloon, and a secondary balloon. The shaft includes at least first and second lumens for delivery of fluid inflation media. The primary balloon has a generally cylindrical wall concentric with the shaft and defining a primary chamber. The primary chamber is in fluid communication with the first lumen for inflation of the primary balloon. The secondary balloon includes an array formed of a plurality of radially disposed inflatable secondary chambers disposed cylindrically about the primary balloon. Each of the secondary chambers is defined by at least an inner wall and an outer wall, the primary balloon wall providing the inner wall for each of the secondary chambers. In this aspect, the invention also includes means to inflate each of the secondary chambers. The means includes a plurality of channels, each channel being in fluid communication with one of the secondary chambers and with the second lumen.

In a narrower embodiment of the catheter in accordance with the invention, the shaft further includes a third lumen, and the catheter further includes a tertiary balloon and means to inflate tertiary chambers of the tertiary balloon. The tertiary balloon includes an array formed of a plurality of radially disposed inflatable tertiary chambers disposed cylindrically about the secondary balloon. Each of the tertiary chambers is defined by at least an inner wall and an outer wall, the secondary chamber outer walls providing the inner walls for the tertiary chambers. The means to inflate each of the tertiary chambers includes a plurality of channels, each channel being in fluid communication with one of the tertiary chambers and with the third lumen.

In another aspect the invention is a method for administering treatment to widen a constricted portion of a bodily conduit to establish a desired blood flow rate through said constricted portion. The method involves inserting a catheter according to one of the embodiments described above into the bodily conduit to position the balloon within the constricted portion. The primary balloon is inflated to a first preselected diameter to engage the constricted portion and to widen the constricted portion to a first treated diameter. The constricted portion is then examined to determine whether the first treated diameter is sufficient to establish the desired blood flow rate. If the first treated diameter is determined not to be sufficient to establish the desired blood flow rate, the secondary chambers are inflated to a second preselected diameter larger than the first preselected diameter.

In an alternate embodiment of the method in accordance with the invention, the shaft further includes a third lumen, and the catheter further includes a tertiary balloon and means for inflating the tertiary chambers of the tertiary balloon. The tertiary balloon includes an array formed of a plurality of radially disposed inflatable tertiary chambers disposed cylindrically about the secondary balloon. Each of the tertiary chambers is defined by at least an inner wall and an outer wall, the secondary chamber outer walls providing the inner walls for the tertiary chambers. The means to inflate each of the tertiary chambers includes a plurality of channels, each channel being in fluid communication with one of the tertiary chambers and with the third lumen. The constricted portion is then examined to determine whether the second treated diameter is sufficient to establish the desired blood flow rate. If the second treated diameter is determined not to be sufficient, the tertiary chambers are inflated to a third preselected diameter larger than the second preselected diameter.

DETAILED DESCRIPTION OF THE PREFERRED EMBODIMENTS

Figure 1:
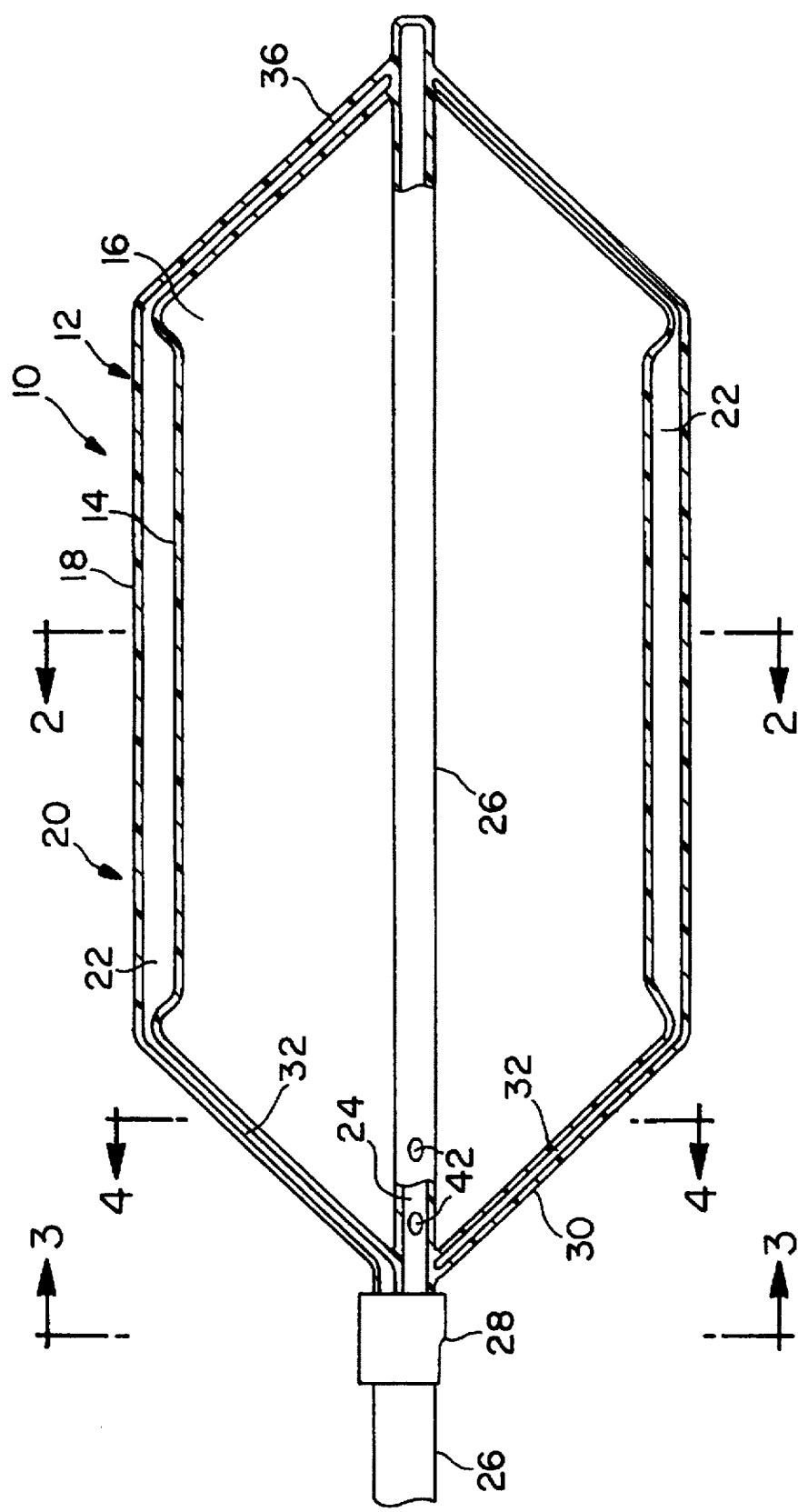
FIG. 1 is a cross-sectional view of a balloon catheter in the inflated condition in accordance with one embodiment of the present invention. The view is taken along the line 1—1 of FIG. 2.

Exemplary embodiments of the catheter in accordance with the invention are described herein. The catheter utilizes a "striped", multi-sized, non-compliant, one-piece balloon in which the balloon wall encloses, in a conventional manner, a primary chamber. The balloon wall is extruded with a cylindrical array of radially disposed, separately inflatable, "stripe-shaped" channels or chambers within the thickness of the balloon wall. As used herein, the terms "striped" and "stripe-shaped" refer to a geometry in which the circumferential width of each in-wall chamber is many times smaller than its axial length. The stripe-shaped channels or chambers in the wall effectively divide the single balloon wall into an inner and one or more outer walls surrounding a plurality of secondary chambers formed by the stripe-shaped channels or chambers. The primary chamber may be inflated to a first, smaller diameter, while the secondary chambers within the balloon wall may be inflated separately from the primary chamber to increase the dilation diameter of the balloon. Thus the balloon described herein provides, in effect, primary (inner) and secondary (outer) balloons, but with the advantages of unitary construction.

The unitary, channeled-wall balloon, therefore, effectively provides the advantages of the above-described double balloon design of the prior art without its disadvantages. The striped shape of the secondary chambers and the unitary fabrication of the striped, multi-sized balloon ensures that any bursting of a balloon will occur in the longitudinal direction, thus simplifying piecing-back of any burst balloon. The piecing-back procedure is therefore no more complicated than the piecing-back of an ordinary single-wall balloon. The striped design also results in differential stiffness about the circumference of the balloon, encouraging regular, multiple-fold collapse of the balloon during deflation, as described in more detail below, and ensuring a smaller diameter for the collapsed balloon.

In operation of, e.g., a double balloon in accordance with one embodiment, the catheter is inserted, and the primary chamber is inflated to a first dilation diameter, engaging and dilating the stenosis. If the dilation is judged to be insufficient, the stripe-shaped secondary chambers are inflated, expanding the balloon to a second dilation diameter. The cylindrical array of secondary chambers thus is equivalent to a secondary balloon surrounding the primary balloon with its single chamber.

To deflate the double balloon before withdrawal of the catheter, the secondary chambers preferably are deflated before the primary chamber, or may be deflated concurrently therewith. The unitary construction of the balloon and the variations in stiffness about its circumference result in multiple folds forming in a regular pattern about the circumference of the balloon wall as the secondary chamber walls collapse. The regular fold pattern, in turn, provides a smaller collapsed profile than is usual with the prior art double balloon design. As mentioned above, this smaller profile can ease passage of the deflated balloon through the arteries during withdrawal of the catheter.

A unitary balloon including the above-described primary chamber and array of secondary balloon chambers may be fabricated by co-extruding a hollow tube of two or more dissimilar polymeric materials using conventional extrusion techniques. A discrete phase, that is a phase which serves as the precursor of the channels (and which dictates their location and shape) is formed of, for example, high density polyethylene, Nylon, low density polyethylene, or polyethylene copolymers. A continuous phase, that is a phase that will form a balloon with the discrete phase enclosed within the walls thereof, can be formed of polyethylene terephthalate or high or low density polyethylene. High density polyethylene, low density polyethylene and polyethylene copolymers can be extruded within polyethylene terephthalate. Nylon can be extruded within a high or low density polyethylene. After the phases are co-extruded, the discrete phase is withdrawn from the continuous phase to leave channels internal to the continuous phase, as described above. Co-extrusion of two plastics materials is well known and conventional techniques are used for such processes. Essential criteria for matching of two polymeric materials for the above-described co-extrusion are that they not adhere to each other after extrusion and that the discrete phase can be withdrawn from the continuous phase leaving channels therein.

While co-extrusion is the preferred method for forming the balloons, it is also possible to extrude tubes having the channels already formed therein using a known type of extrusion die. The thickness of the precursors to the channels is extremely small, typically about 0.025–0.5 mm within a tube having a total wall thickness between about 0.07 and 1.0 mm and outside diameter between about 0.25 and 5.0 mm. Therefore, extrusion with the desired preformed channels is more difficult than co-extrusion; thus co-extrusion is preferred.

Following the fabrication of the balloon, secondary chambers may be fabricated from the channels in the balloon wall by, for example, heating the tube-shaped extruded balloon only in the area where the secondary chambers are desired to a temperature sufficient to soften the balloon in that area to permit stretching of the balloon walls. The primary and secondary chambers are then pressurized simultaneously to expand the chambers to the desired diameters.

Referring now to FIG. 1, the catheter 10 of the present invention includes double balloon 12 in which inner balloon wall 14 encloses primary chamber 16. Outer balloon wall 18 cooperates with inner balloon wall 14 to enclose inflatable cylindrical array 20 of radially disposed secondary chambers 22. Primary chamber 16 is in fluid flow relation with inflation lumen 24 disposed in shaft 26. Each of secondary chambers 22 in array 20 is in fluid flow relation with an additional inflation lumen disposed in shaft 26, as will be explained hereinafter. Hub 28 is disposed around shaft 26 to secure the assembly. Proximal intermediate member 30 connects hub 28 with double balloon 12. Channels 32 are formed in proximal intermediate member 30 to provide fluid passageways between additional inflation lumen 34 within shaft 26 and the interiors of secondary chambers 22. Inflation lumens 24 and 34 may be two of several lumens in shaft 26 as will be explained hereinafter.

Double balloon 12 is also connected to distal intermediate member 36. In the herein depicted embodiment shaft 26 is disposed centrally within primary chamber 16 and array 20 to provide support for double balloon 12 by means of distal intermediate member 36. In other embodiments, not shown, the shaft is terminated at hub 28 and double balloon 12 and distal intermediate member 36 are self supporting.

Inflation of primary chamber 16 causes inner balloon wall 14 to expand from a folded arrangement around shaft 26 to being spaced therefrom. This expansion causes proximal and distal intermediate members 30 and 36 to assume generally conical shapes and allow for an increase in the diameter of balloon 12 and for pressing of the balloon against the lesion being addressed. If necessary, secondary chambers 22 can be inflated, causing outer balloon wall 18 of array 20 to expand from a folded arrangement around inner wall 14 and primary chamber 16 to being spaced therefrom. This expansion of chambers 22 allows for a further increase in the diameter of double balloon 12 and further expansion of the stenosis. In its collapsed state the profile of balloon 12 can approximate the diameter of shaft 26 because an extremely thin walled balloon can be employed, as will be described hereinafter.

Figure 2:
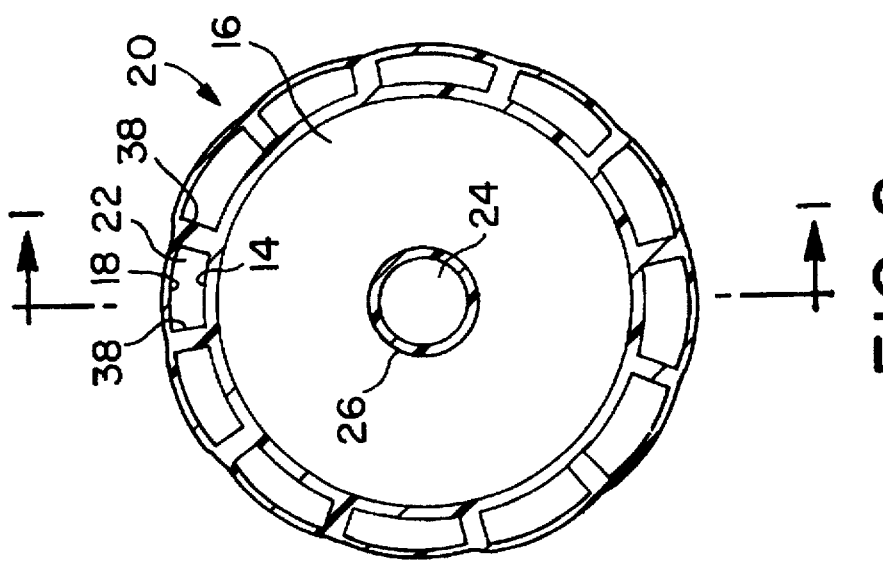
FIG. 2 is a cross-sectional view of the catheter shown in FIG. 1 taken along the line 2—2.

Referring now to FIG. 2, secondary chambers 22 are shown in an inflated state. Each of the secondary chambers has side walls 38, inner wall 14, and outer wall 18. Chambers 22 are disposed in cylindrical array 20 around an axis which can be shaft 26. Each of chambers 22 share a common side wall, wall 38, with the next adjacent of chambers 22, to enable the expansion of chambers 22 into array 20 upon inflation. In FIG. 2 proximal intermediate member 30 is not shown to provide for a simplified depiction of the invention.

Figure 3:
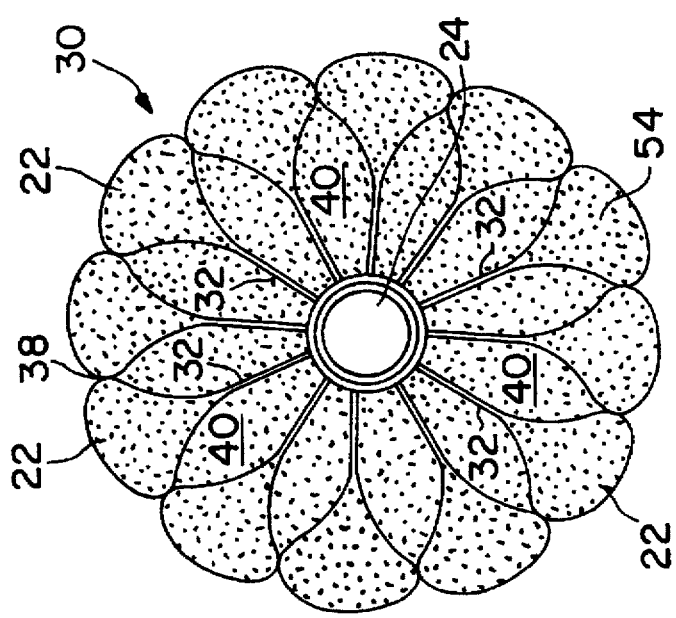
FIG. 3 is an end view of the catheter of FIG. 1 showing the relative dispositions of the array of secondary chambers, webs, and channels in the proximal end of the catheter. The view is taken along the line 3—3 of FIG. 1.

A typical balloon diameter when only the primary balloon chamber is fully inflated is about 0.04–2 in; when the secondary chambers are also inflated the diameter range typically is about 0.06–2.5 in. (The diameter of primary chamber 16, when inflated, is typically about 0.04–2.0 in.) The wall thickness of each of walls 14, 18, and 38 typically is about 0.0001–0.004 in, with 0.0003–0.002 in being preferred. The deflated profile of double balloon 12 typically is about 0.03–2.5 in. Referring to FIG. 3, the proximal end of the catheter assembly, that is proximal intermediate member 30, is shown. Each of secondary chambers 22 are arrayed cylindrically around the axis of the catheter. Each of side walls 38 of chambers 22 is an integral part of an adjacent side wall 38 of an adjacent chamber 22. Each of chambers 22 is connected to a supply of inflation fluid by means of a channel, as 32, formed within proximal intermediate member 30. Channels 32 are separated from each other by webs 40 which form integral parts of proximal intermediate member 30. Each of channels 32 in the proximal intermediate member terminate in a central manifold area 42 in the region of hub 28, as shown in FIG. 1.

Distal intermediate member 36 (FIG. 1) can be a mirror image configuration of proximal intermediate member 30, except inflation media normally is carried within channels formed in only one intermediate member, preferably the proximal intermediate member.

Figure 4:
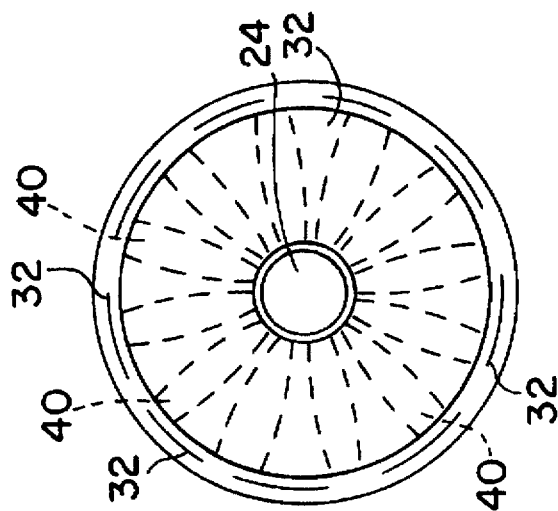
FIG. 4 is a cross-sectional interior view of the array of secondary chambers taken along the line 4—4 of FIG. 1.

In FIG. 4, a cross-sectional view is shown of the interior of proximal intermediate member 30. Channels 32 are shown as dotted lines within body of webs 40 and as solid lines within the cross-section of the balloon wall. Each of channels 40 is connected to additional inflation lumen 34 (shown in FIG. 5) of shaft 26 so that inflation media can be delivered to secondary chambers 22. A mirror image configuration can be embodied in distal intermediate member 36, except that channels 32 to carry inflation media are not necessary in both the proximal and distal intermediate members.

Figure 5:
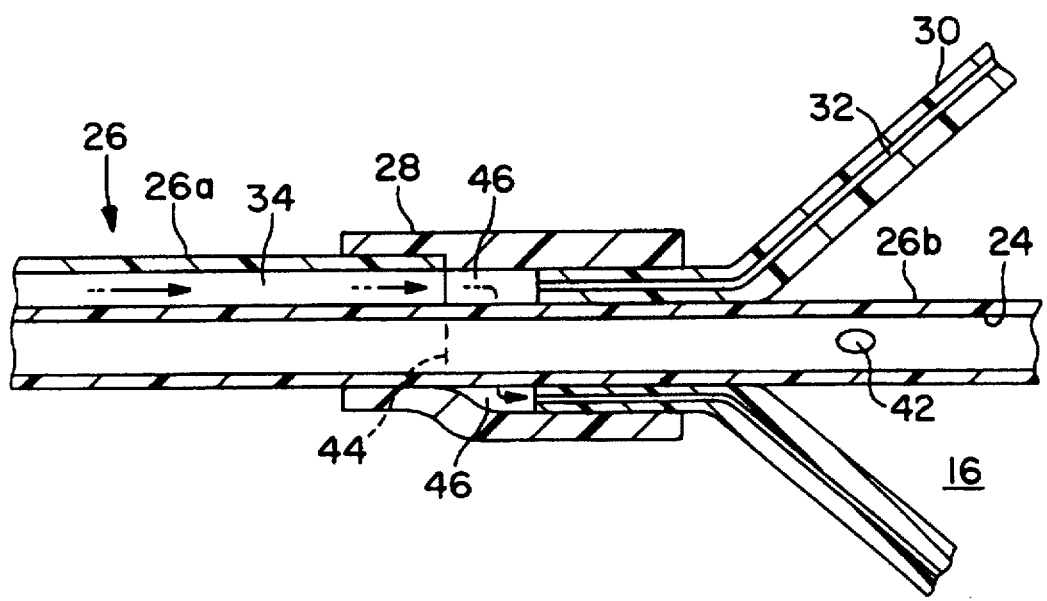
FIG. 5 is an enlarged cross-sectional view of a portion of the catheter of FIG. 1 showing particularly the fluid connection of the chambers to lumens in the shaft.

Referring now to FIG. 5, a joint is shown between proximal intermediate member 30 and shaft 26 with inflation lumens 24 and 34. Shaft 26 can be formed with a major lumen, as 24, and a minor lumen, as 34. Minor lumen 34 carries the inflation fluid to channels 32 in proximal intermediate member 30 (which in turn relays the fluid to the array of secondary chambers). Major lumen 24 carries the inflation fluid to primary chamber 16, for example via at least one port 42. Shaft 26 can extend within the interior of the primary chamber to hold a guidewire that extends from the distal tip of the shaft (not shown, but as conventional in the art, for example via a separate lumen).

In the embodiment shown in FIG. 5, shaft 26 is formed with two segments, one, 26a, terminating at the end of minor lumen 34 and being joined, without minor lumen 34, to another shaft segment, 26b, of similar dimensions at joint 44. Hub 28, for example, of shrinkable plastic is attached both to shaft 26 and to the outside of the end of the proximal intermediate member 30. Manifold 46 is formed between the opening between the end of minor lumen 34 and the end of proximal intermediate member 30. Inflation fluid flowing from minor lumen 34 enters into manifold 46 and thence to channels 32 and ultimately to secondary chambers 22 (not shown in FIG. 5) to inflate them. Sealing segments 26a and 26b of the shaft together and sealing the shaft to hub 28 and to the end of proximal intermediate member 30 is in accordance with conventional techniques used in the art for sealing such elements together.

Figure 6:
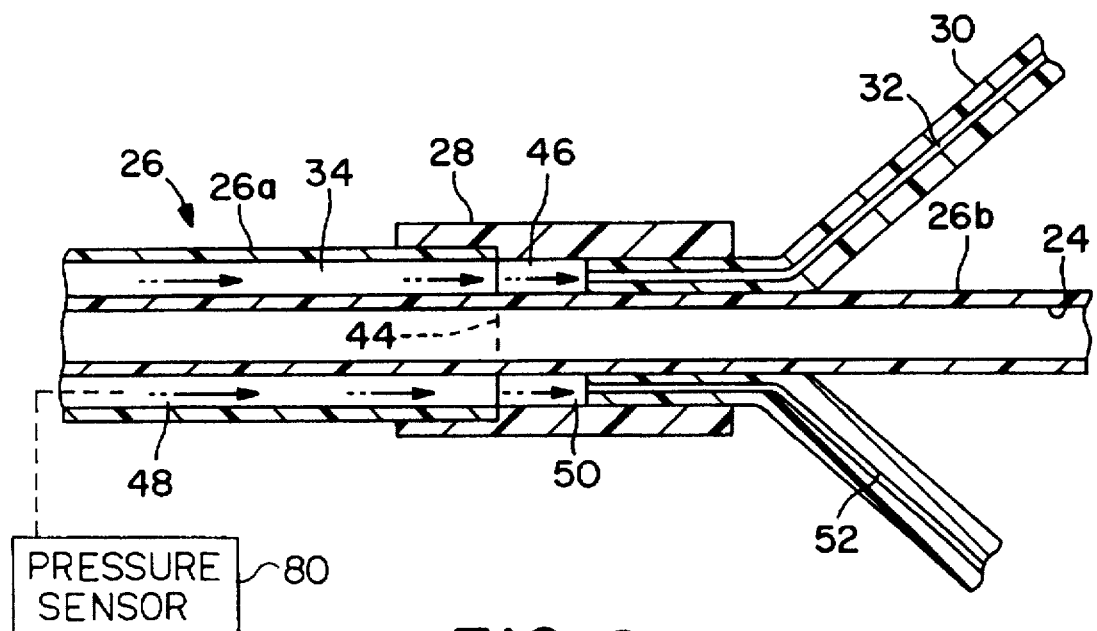
FIGS. 6 and 7 are enlarged cross-sectional views of the fluid-connection portions of alternate embodiments of the catheter in accordance with the invention.

Another embodiment is shown in FIG. 6, in which like features to those shown in FIG. 5 are indicated by the same reference numerals. Shaft 26 is formed with two segments, one, 26a, terminating at the end of minor lumens 34 and 48 and being joined, without minor lumens 34 and 48, to another shaft segment, 26b, of similar dimensions at joint 44. Hub 28 is attached both to shaft 26 and to the outside of the end of the proximal intermediate member 30. First manifold 46 is formed between the opening between the end of minor lumen 34 and the end of proximal intermediate member 30. Inflation fluid flowing from minor lumen 34 enters into first manifold 46 and thence to channels 32 and ultimately to secondary chambers 22 (shown in FIGS. 1 and 3) to inflate them. Second manifold 50 is formed between the opening between the end of minor lumen 48 and the end of proximal intermediate member 30. Inflation fluid flowing from minor lumen 48 enters into second manifold 50 and thence to channel 52 and ultimately to secondary chamber 54 (shown in FIG. 3) to inflate it. Chamber 54 is in fluid communication via channel 52, manifold 50 and lumen 48 with a conventional pressure sensing means 80, for example a pressure transducer. Sealing segments 26a and 26b of the shaft together and sealing the shaft to hub 28 and to the end of proximal intermediate member 30 is in accordance with conventional techniques used in the art for sealing such elements together.

The catheter shown in FIG. 6 operates similarly to that of FIG. 5. In addition, the pressure sensing means may be used to measure the pressure in chamber 54, thus indicating the force (compression resistance) exerted on the balloon by the stenosis being treated. This measurement may be used to evaluate the characteristics of pre- and post-dilation lesions and to refine the dilation procedure to prevent restenosis. In operation, pressure sensing secondary chamber 54 is inflated to a pressure lower than that used for the dilation procedure. A typical inflation pressure in chamber 54 for this pressure measuring procedure is about 1 atm. The primary chamber is then inflated, as described above, and the resulting increase in the pressure within secondary chamber 54 is monitored. This increase in pressure may be compared to a similar reading taken in a normal vessel, and is directly related to the resistance to expansion in the stenosis. The above-described pressure sensing procedure utilizes a single secondary chamber for pressure measurement. Alternatively, a plurality or all of the secondary chambers may be in fluid communication with lumen 48 to provide more than one pressure sensing chamber. Also alternatively, the balloon may be inserted to overlap both a stenosis and healthy vessel tissue to give the stress characteristics of each simultaneously.

In an alternate embodiment, a catheter similar to that illustrated in FIG. 6 (with or without the pressure sensing means) and having similarly interconnected secondary chambers, channels, manifolds, and lumens may be used to provide three or more progressively larger inflation diameters for the balloon. In such a catheter, inflation fluid flows from minor lumen 34 to one or more secondary chambers 22 via manifold 46 and one or more channels 32, while a second supply of inflation fluid flows from minor lumen 48 into one or more secondary chambers 54 via manifold 50 and one or more channels 52. Thus, the balloon may be sequentially inflated: to a first diameter by inflating the primary chamber, to a second, larger diameter by inflating the one or more secondary chambers 22, and to a third, still larger diameter by inflating the one or more secondary chambers 54. Preferably, chambers 22 and chambers 54 each extend approximately half way about the circumference of the balloon. Alternatively, three or more separately inflatable sets of secondary chambers with associated channels, manifolds, and lumens may be provided, and/or an additional arrangement of multiple sets of tertiary chambers with associated inflation means may be added.

Figure 7:
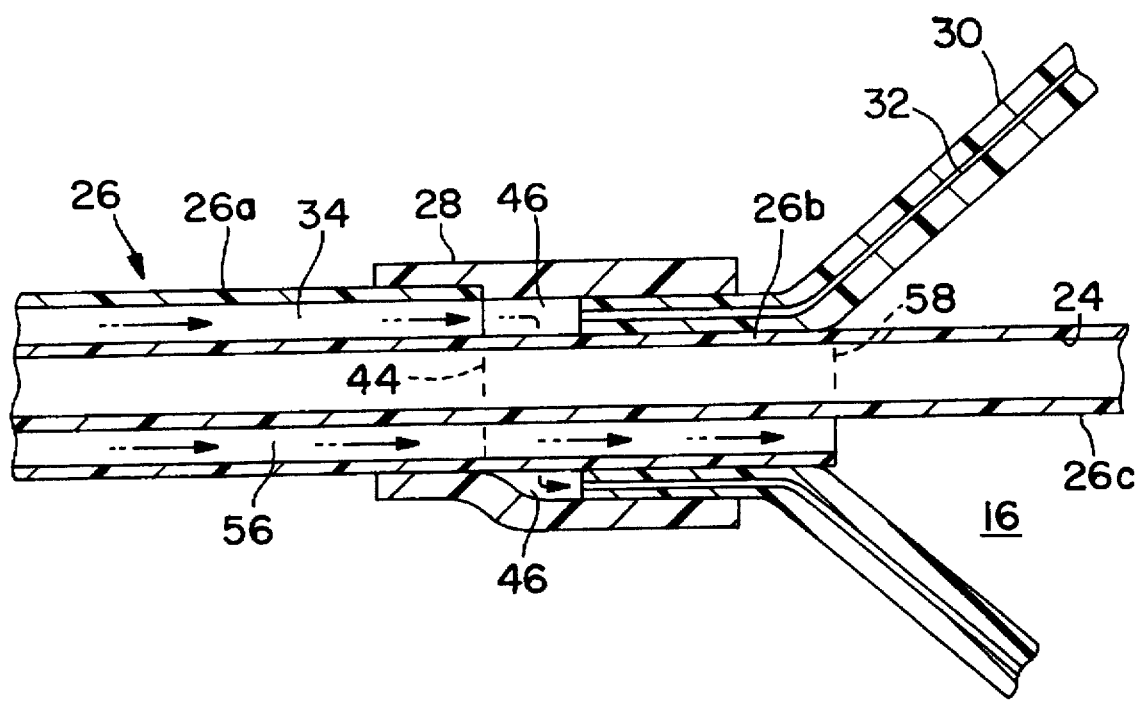

FIG. 7 illustrates an alternate means of inflating the primary chamber utilizing a lumen separate from the major lumen of the shaft. In FIG. 7, like features to those shown in FIGS. 5 and 6 are indicated by the same reference numerals. Shaft 26 is formed with three segments, one, 26a, terminating at the end of minor lumen 34 and being joined, without minor lumen 34, to another shaft segment, 26b, of similar dimensions at joint 44. Hub 28 is attached both to shaft 26 and to the outside of the end of the proximal intermediate member 30. First manifold 46 is formed between the opening between the end of minor lumen 34 and the end of proximal intermediate member 30. Inflation fluid flowing from minor lumen 34 enters into first manifold 46 and thence to channels 32 and ultimately to secondary chambers 22 (shown in FIGS. 1 and 3) to inflate them. Inflation fluid flowing from second minor lumen 56 enters primary chamber 16 to inflate it. Sealing segments 26a, 26b, and 26c of the shaft together and sealing the shaft to hub 28 and to the end of proximal intermediate member 30 is in accordance with conventional techniques used in the art for sealing such elements together. Major lumen 24 may then be utilized for other known purposes, such as carrying of a guide wire.

Figure 8:
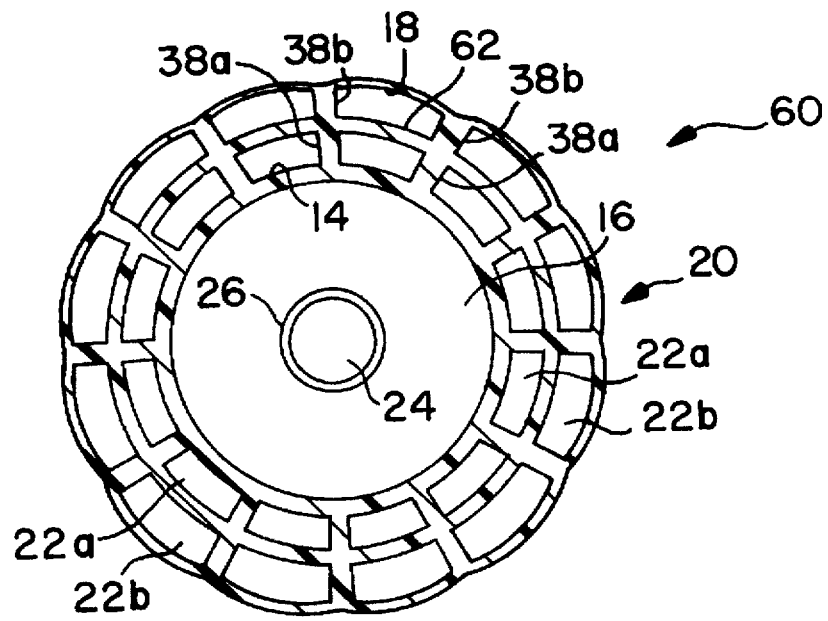
FIGS. 8 and 9 are cross-sectional views of triple balloon catheters in accordance with alternate embodiments of the invention.

FIG. 8 illustrates a triple balloon in accordance with one embodiment of the invention. Like features to those shown in FIG. 2 are indicated by the same reference numerals. As shown in FIG. 8, triple balloon 60 includes inner balloon wall 14 enclosing primary chamber 16. Intermediate balloon wall 62 and outer balloon wall 18 cooperate with inner balloon wall 14 to enclose inflatable double-cylindrical array 20 of radially disposed secondary chambers 22a and 22b respectively. (In effect, secondary chambers 22b serve as "tertiary" chambers surrounding "secondary" chambers 22a) Primary chamber 16 is in fluid flow relation with inflation lumen 24 disposed in shaft 26, as hereinbefore described. Each of secondary chambers 22a in array 20 is in fluid flow relation with an additional inflation lumen (not shown) disposed in shaft 26 in a similar manner to that illustrated in FIG. 5. Similarly, each of secondary chambers 22b in the array is in fluid flow relation with another additional inflation lumen (not shown) disposed in shaft 26. The assembly is secured by a hub similarly to the embodiments illustrated above. Typically, proximal and distal intermediate members (not shown) connect triple balloon 60 to the shaft. Channels (not shown) formed in the proximal intermediate member provide fluid passageways between the additional inflation lumens and the interiors of secondary chambers 22a and 22b.

After inflation of primary chamber 16, inflation of secondary chambers 22a causes intermediate balloon wall 62, carrying collapsed outer balloon wall 18, to expand from a folded arrangement around inner wall 14 and primary chamber 16 to being spaced therefrom, in a manner similar to that described before for double balloon 12. This expansion allows for an increase in the diameter of balloon 60 and for further pressing of the balloon against the lesion being addressed. If the diameter of balloon 60 is still not deemed sufficient, secondary chambers 22b may be inflated, causing outer balloon wall 18 to expand from its folded arrangement around intermediate wall 62 and increasing the diameter of balloon 60 still further. In its collapsed state the profile of triple balloon 60 can approximate the diameter of shaft 26 because of its folded arrangement and because an extremely thin walled balloon can be employed.

In FIG. 8, secondary chambers 22a and 22b are shown in an inflated state. Each of secondary chambers 22a and 22b has side walls and "inner" and "outer" walls, similarly to the geometry of chambers 22 of balloon 12. Chambers 22a are defined by inner wall 14, intermediate wall 62, and side walls 38a; chambers 22b, by intermediate wall 62, outer wall 18, and side walls 38b. Chambers 22a and 22b are disposed in double-cylindrical array 20 around an axis, which can be shaft 26. Each of chambers 22a share a common side wall, wall 38a, with the next adjacent of chambers 22a; each of chambers 22b share a common side wall, 38b, with the next adjacent of chambers 22b. In the embodiment shown in FIG. 8, each of chambers 22a also shares a common wall, intermediate wall 62, with only one of chambers 22b, side walls 38a and 38b being aligned radially with one another.

Figure 9:
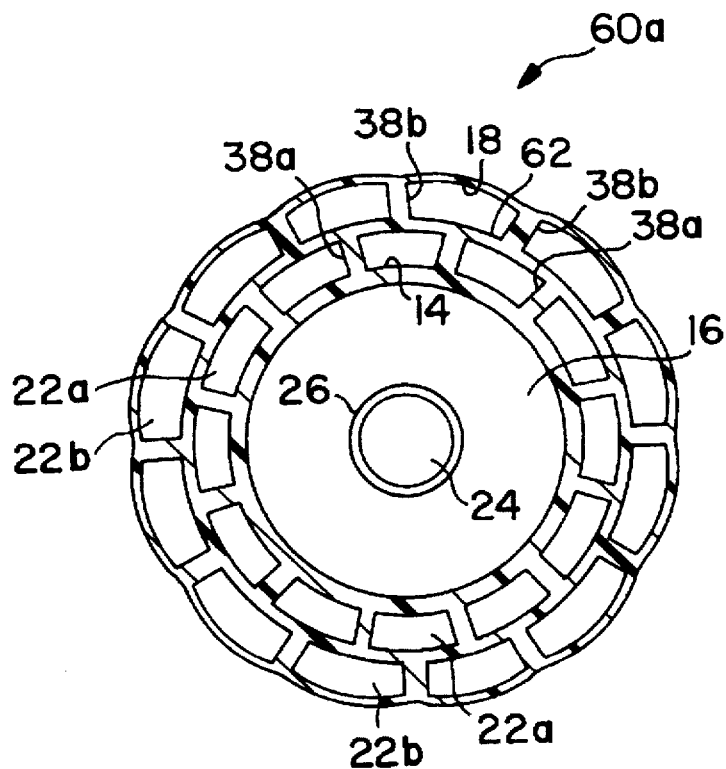

An alternate embodiment of a triple balloon, balloon 60a, is illustrated in FIG. 9, in which like features to those of FIG. 8 are indicated by the same reference numerals. In FIG. 9, side walls 38a and 38b are not aligned radially, but are in a staggered arrangement, and the portion of intermediate wall 62 enclosing each chamber 22a is shared with two chambers 22b. Of course, other arrangements of the inner and outer secondary chambers of a triple balloon are possible, and are within the scope of this invention.

Figure 12:
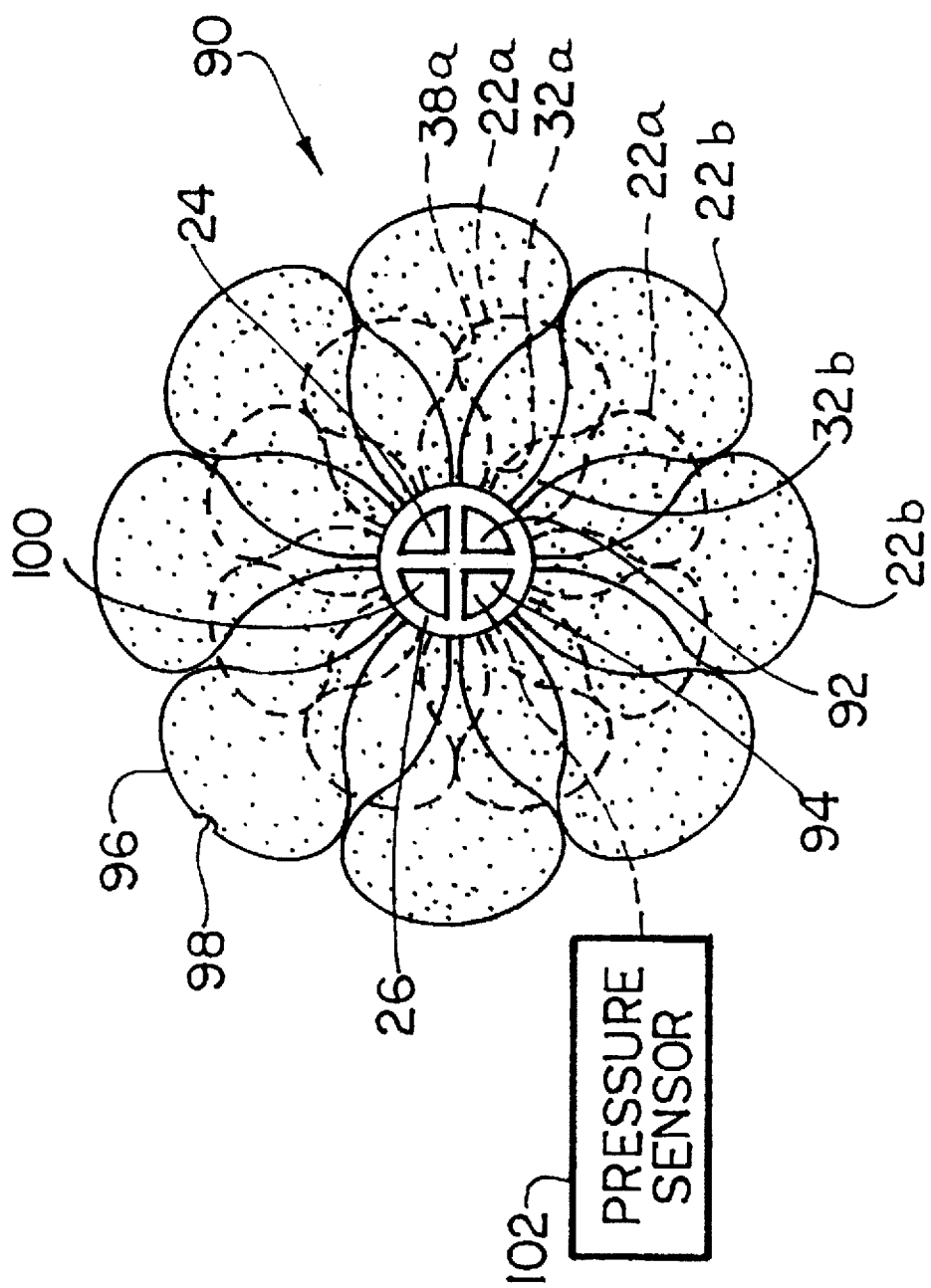
FIG. 12 is an end view of the catheter of FIG. 9, showing the relative dispositions of the array of secondary chambers, tertiary chambers, webs, and channels in the proximal end of the catheter.

FIG. 12 illustrates proximal intermediate member 90 of catheter balloon 60a of FIG. 9. Like features to those shown in FIG. 9 are indicated by the same reference numerals. Secondary chambers 22a are arrayed cylindrically around the axis of the catheter. Each side wall 38a is shared by two adjacent secondary chambers 22a. Each of chambers 22a is connected to a supply of inflation fluid by means of a channel, as 32a, within proximal intermediate member 90. Each of channels 32a terminate at shaft 26, and are in fluid flow relation with second, inflation lumen 92. In a manner similar to that described for FIGS. 8 and 9, tertiary chambers 22b are arrayed cylindrically around the axis of the catheter, radially adjacent to chambers 22a. Each side wall 38b is shared by two adjacent tertiary chambers 22b, and intermediate wall 62 is shared between chambers 22a and 22b, as described for the balloon of FIG. 9. Each of chambers 22b is connected to a supply of inflation fluid by means of a channel, as 32b, within proximal intermediate member 90. Each of channels 32b terminate at shaft 26, and are in fluid flow relation with third, inflation lumen 94.

Figure 11:
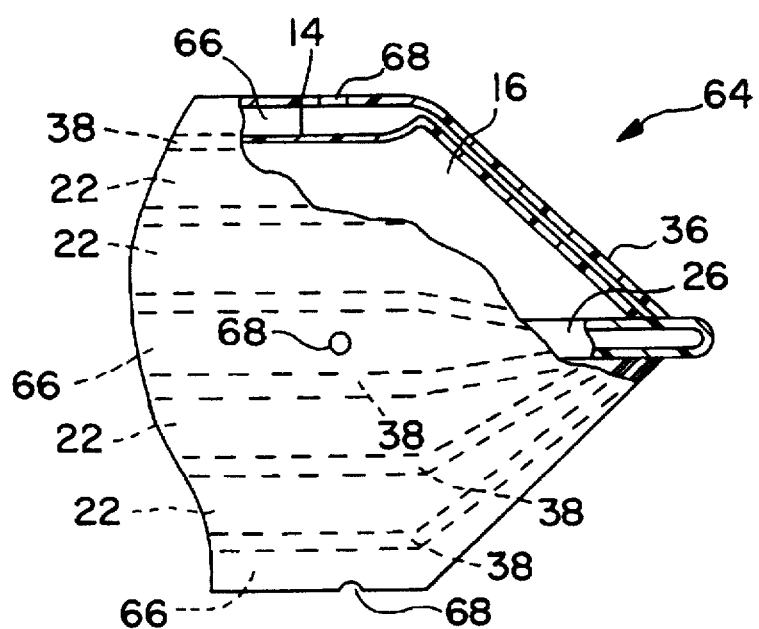
FIG. 11 is an elevation view, partly in cross-section, of a balloon adapted for delivering medication.

If desired, one or more of chambers 22b may serve as medication dispensing conduits, similar to conduits 66 of FIG. 11. Conduit 96 is provided with aperture 98 to serve for dispensing of medication supplied from a source of medication (not shown) via fourth lumen 100. Also if desired, chambers 22b may be in fluid communication with conventional pressure sensing means 102, similar to means 80 shown in FIG. 6, via channels 32b and lumen 94.

The distal intermediate member of balloon 60a may be a mirror image configuration of proximal intermediate member 90, except inflation media normally is carried within channels formed in only one intermediate member, preferably the proximal intermediate member.

Figure 10:
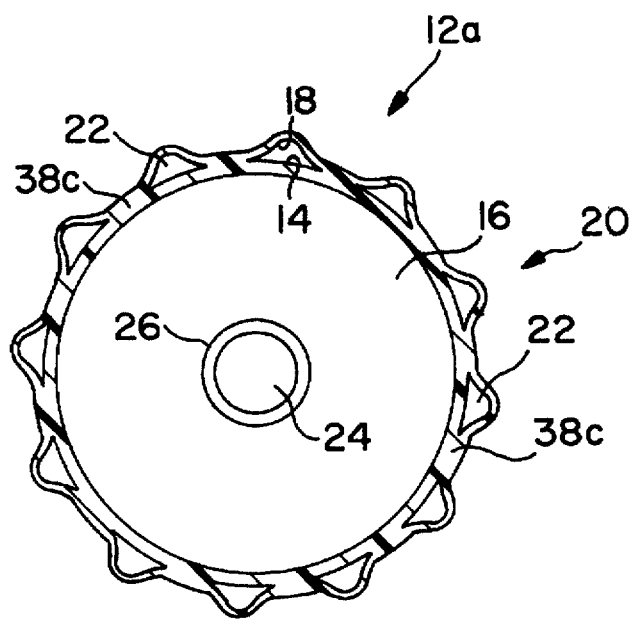
FIG. 10 is a cross-sectional view of a double balloon catheter in accordance with an alternate embodiment of the invention.

An alternate embodiment of a double balloon is shown in FIG. 10, in which like features to those shown in FIG. 2 are indicated by the same reference numerals. In FIG. 10, secondary chambers 22 of double balloon 12a are disposed in cylindrical array 20 around an axis which can be shaft 26. Each of chambers 22 share a common "connector" wall, wall 38c, with the next adjacent of chambers 22. Thus, in this embodiment, inner wall 14 and outer wall 18 are each present as segments joined by connector wall 38c. During manufacture, outer wall 18 of each of chambers 22 is stretched more than inner wall 14 to enable the expansion of chambers 22 into array 20 upon inflation. This gives balloon 12a a more ridged appearance than balloon 12 when inflated, and results in an outer wall, 18, that will fold readily against inner wall 14 to minimize the diameter of the deflated balloon. Each of chambers 22 is connected to a supply of inflation fluid by means of a channel (not shown) formed within the proximal intermediate member (also not shown), as described hereinbefore.

In yet another embodiment, the balloons described herein are adapted for concurrent or sequential angioplasty and delivery of medication. The adaptation is similar to that described in above-referenced U.S. patent application Ser. No. 07/862,415, incorporated herein by reference. For example, one or some of the secondary chambers of a balloon similar to double balloon 12 of FIGS. 1–4 may serve as conduits for delivery of medication, being in fluid communication with a medication source via an additional lumen, for example in a manner similar to that shown for pressure measurement in FIG. 6. Alternatively, one or some of the secondary chambers may contain medication which is "squeezed" out of the chamber on inflation of the primary chamber.

A balloon adapted for delivering medication is illustrated in FIG. 11, in which features similar to those shown in FIG. 1 are indicated by the same reference numerals. In FIG. 11, dilating and medication dispensing balloon 64 includes primary chamber 16 and secondary chambers 22, providing a balloon catheter expandable to either of two different diameters, as described hereinabove. Adjacent chambers 22 share common side walls 38, as described above. Some of secondary chambers 22 are adapted to serve as medication dispensing conduits 66. Chamber 16 and non-dispensing chambers 22 are in fluid communication with first and second lumens (not shown in FIG. 11) for inflation, in the manner hereinbefore described. Conduits 66 can be supplied with medication from a medication source (not shown) via a separate lumen, for example as described in U.S. patent application Ser. No. 07/862,415. In the embodiment shown in FIG. 11, each conduit 66 is provided with an aperture 68 for introduction of medication into a bodily organ, for example a blood vessel, that has been catheterized. Concurrently or sequentially, chamber 16 and, if necessary, chambers 22 may be inflated sufficiently for a dilation procedure. While FIG. 11 shows apertures 68 disposed in a circumferential array near distal intermediate member 36, other configurations that enable introduction of medication into the desired area may be used. For example, a helical array of dispensing apertures and the dispensing of medication directly from the conduit ends where they rejoin the catheter shaft are both disclosed in U.S. patent application Ser. No. 07/862,415. Conduits 66 may be the same cross-sectional size and/or shape as channels 22, or may be of different size and/or shape. In an alternate embodiment, a triple balloon, as shown in FIGS. 8 and 9, may be adapted such that one, some, or all of chambers 22b provide the desired dispensing conduits.

In one method for manufacturing the double or triple balloon in accordance with the present invention, two or more dissimilar materials are co-extruded to form a tube. Such dissimilar materials have been described above. For example, one phase, a continuous phase, may be formed of polyethylene terephthalate; a second, discrete phase within the continuous phase is formed of a material such as high density polyethylene. This discrete phase can be withdrawn from the continuous phase, thus forming a tube (in this example polyethylene terephthalate) with a plurality of open channels within its wall. For the above-described double balloon, the discrete phase is extruded such that the secondary chambers within the inflated balloon are disposed to define a single-cylinder array, as shown in FIG. 2 or FIG. 10. In the inflated triple balloon, the secondary chambers define an array of two coextensive, concentric cylinders, as shown in FIG. 8 or FIG. 9. The shape and arrangement of the secondary chambers can be varied as desired by the operator by varying the design of the extrusion die.

The primary chamber of the balloon is then shaped, for example by heating and inflation, in known manner. However, the secondary chambers also must be shaped, for example, by heating the tubing only in the predetermined area where the secondary chambers are to be formed (i.e. not in the area of the proximal and distal intermediate portions), then pressurizing simultaneously both this secondary chamber area and the interior of the balloon, that is the primary chamber, to expand the secondary chambers to the desired diameter. The proximal and distal intermediate members are formed by keeping the primary chamber in each of these areas, either simultaneously or sequentially, heated and inflated while not pressurizing the secondary chambers. In that way the channels, as 32, will expand minimally, but the spaces between the individual channels can be stretched and widened sufficiently to form webs to achieve the desired, typically conical, shape in the proximal and distal intermediate members.

It is apparent that modifications and changes can be made within the spirit and scope of the present invention. It is our intention, however, only to be limited by the scope of the appended claims.

We claim:

1. A catheter for insertion into a bodily conduit, said catheter comprising:
    a shaft comprising at least first and second lumens for delivery of fluid inflation media;
    a primary balloon having a generally cylindrical wall concentric with said shaft and defining a primary chamber, said primary chamber being in fluid communication with said first lumen for inflation of said primary balloon;
    a secondary balloon comprising an array formed of a plurality of radially disposed inflatable secondary chambers disposed cylindrically about said primary balloon, wherein each of said secondary chambers has a proximal end and is defined by at least an inner wall and an outer wall, said primary balloon wall providing said inner wall for each of said secondary chambers;
    means to inflate each of said secondary chambers, said means including a plurality of channels, wherein each of said channels is in fluid communication with one of said secondary chambers and with said second lumen, said channels extend into said proximal ends of each of said secondary chambers, and circumferential webs separate said channels from each other.

2. A catheter in accordance with claim 1 wherein each of said secondary chambers is further defined by side walls, each of said secondary chambers sharing a common one of said side walls with an adjacent one of said secondary chambers.

3. A catheter in accordance with claim 1 wherein said channels and said webs together form a conical proximal intermediate member attached to said primary and said secondary balloons.

4. A catheter in accordance with claim 3 further including a conical distal intermediate member attached to said primary and said secondary balloons.

5. A catheter in accordance with claim 4 wherein said shaft extends through both of said proximal and said distal intermediate members.

6. A catheter in accordance with claim 3 wherein said fluid communication between said channels and said second lumen is provided by a manifold formed between said channels and said second lumen; and wherein said proximal intermediate member is joined to said shaft by a hub, and a void space between said hub, said first lumen, said second lumen, and said channels defines said manifold.

7. A catheter in accordance with claim 1 wherein said fluid communication between said channels and said second lumen is provided by a manifold formed between said channels and said second lumen.

8. A catheter in accordance with claim 1 further comprising a medication dispensing lumen, and wherein at least one of said secondary chambers is in fluid communication with said bodily conduit and with a source of fluid medication via said medication dispensing lumen, thereby providing a dispensing conduit for the delivery of medications to predetermined locations within said bodily conduit.

9. A catheter in accordance with claim 1 wherein said channels are primary channels, and said shaft further comprises a third lumen; and further comprising:
    a tertiary balloon comprising an array formed of a plurality of radially disposed inflatable tertiary chambers disposed cylindrically about said secondary balloon; wherein each of said tertiary chambers is defined by at least an inner wall and an outer wall, said secondary chamber outer walls providing said inner walls for said tertiary chambers; and
    means to inflate each of said tertiary chambers, said means including a plurality of secondary channels, each secondary channel being in fluid communication with one of said tertiary chambers and with said third lumen.

10. A catheter in accordance with claim 9 wherein each of said tertiary chambers is further defined by side walls, each of said tertiary chambers sharing a common one of said side walls with an adjacent one of said tertiary chambers.

11. A catheter in accordance with claim 9 wherein said third lumen is in fluid communication with a pressure sensing means for monitoring the inflation pressure in at least one of said tertiary chambers.

12. A catheter in accordance with claim 11 wherein said shaft further comprises a fourth lumen, at least one of said tertiary chambers being in fluid communication with said third lumen and at least another of said tertiary chambers being in fluid communication with said fourth lumen.

13. A catheter in accordance with claim 9 further comprising a medication dispensing lumen, and wherein at least one of said tertiary chambers is in fluid communication with said bodily conduit and with a source of fluid medication via said medication dispensing lumen, thereby providing a dispensing conduit for the delivery of medications to predetermined locations within said bodily conduit.

14. A catheter for insertion into a bodily conduit, said catheter comprising:
    a shaft comprising at least first and second lumens for delivery of fluid inflation media;
    a primary balloon having a generally cylindrical wall concentric with said shaft and defining a primary chamber, said primary chamber being in fluid communication with said first lumen for inflation of said primary balloon;

a secondary balloon comprising an array formed of a plurality of radially disposed inflatable secondary chambers disposed cylindrically about said primary balloon, wherein each of said secondary chambers is defined by at least an inner wall and an outer wall, said primary balloon wall providing said inner wall for each of said secondary chambers; and means to inflate each of said secondary chambers, said means including a plurality of channels, each channel being in fluid communication with one of said secondary chambers and with said second lumen;

wherein said second lumen is in fluid communication with a pressure sensing means for monitoring the inflation pressure in at least one of said secondary chambers.

15. A catheter in accordance with claim 14 wherein said shaft further comprises a third lumen, at least one of said secondary chambers being in fluid communication with said second lumen and at least another of said secondary chambers being in fluid communication with said third lumen.

16. A catheter for insertion into a bodily conduit, said catheter comprising:

a shaft comprising at least first and second lumens for delivery of fluid inflation media;

a primary balloon having a generally cylindrical wall concentric with said shaft and defining a primary chamber, said primary chamber being in fluid communication with said first lumen for inflation of said primary balloon;

a secondary balloon comprising an array formed of a plurality of radially disposed inflatable secondary chambers disposed cylindrically about said primary balloon, wherein each of said secondary chambers has a proximal end and is defined by at least an inner wall and an outer wall, said primary balloon wall providing said inner wall for each of said secondary chambers;

means to inflate at least one of said secondary chambers, said means including at least one first channel in fluid communication with said at least one secondary chamber and with said second lumen, wherein said at least one first channel extends into said proximal end of at least one of said secondary chambers;

a plurality of additional channels each in fluid communication with one of the remainder of said secondary chambers, wherein each of said additional channels extends into said proximal end of one of said remainder of said secondary chambers, and circumferential webs separate said first and said additional channels from each other.

17. A catheter in accordance with claim 16 wherein said shaft further comprises a third lumen, said at least one secondary chamber being in fluid communication with said second lumen and at least said one of said remainder of said secondary chambers being in fluid communication with said third lumen; wherein said second lumen is in fluid communication with a pressure sensing means for monitoring the inflation pressure in said at least one secondary chamber.

18. A catheter in accordance with claim 16 wherein said shaft further comprises a third lumen; and further comprising:

a tertiary balloon comprising an array formed of a plurality of radially disposed inflatable tertiary chambers disposed cylindrically about said secondary balloon; wherein each of said tertiary chambers is defined by at least an inner wall and an outer wall, said secondary chamber outer walls providing said inner walls for said tertiary chambers; and means to inflate at least one of said tertiary chambers, said means including at least one channel in fluid communication with said at least one tertiary chamber and with said third lumen.

19. A catheter in accordance with claim 18 further comprising pressure sensing means in fluid communication with said third lumen for monitoring the inflation pressure in said at least one tertiary chamber.

20. A catheter in accordance with claim 19 wherein said shaft further comprises a fourth lumen, said at least one tertiary chamber being in fluid communication with said third lumen and at least another of said tertiary chambers being in fluid communication with said fourth lumen.

21. A catheter in accordance with claim 16 wherein said shaft further comprises at least a third lumen for delivery of fluid inflation media; each of said remainder of said secondary chambers being in fluid communication through its associated channel with said third lumen.

22. A catheter in accordance with claim 21 wherein said fluid communication between said first channel and said second lumen is provided by a first manifold formed between said first channel and said second lumen, and said fluid communication between said additional channels and said third lumen is provided by a second manifold formed between said additional channels and said third lumen.

23. A method for administering treatment to widen a constricted portion of a bodily conduit to establish a desired blood flow rate through said constricted portion, said method comprising the steps of:

inserting a catheter having an inflatable balloon into said bodily conduit to position said balloon within said constricted portion, said catheter comprising a shaft comprising at least first and second lumens for delivery of fluid inflation media; a primary balloon having a generally cylindrical wall concentric with said shaft and defining a primary chamber, said primary chamber being in fluid communication with said first lumen for inflation of said primary balloon to a first preselected diameter; a secondary balloon comprising an array formed of a plurality of radially disposed inflatable secondary chambers disposed cylindrically about said primary balloon, wherein each of said secondary chambers is defined by at least an inner wall and an outer wall, said primary balloon wall providing said inner wall for each of said secondary chambers; means to inflate each of said secondary chambers to achieve a second preselected diameter greater than said first preselected diameter, said means including a plurality of channels, each channel being in fluid communication with one of said secondary chambers and with said second lumen;

inflating said primary balloon to said first preselected diameter to engage said constricted portion and to widen said constricted portion to a first treated diameter;

examining said constricted portion to determine whether said first treated diameter is sufficient to establish said desired blood flow rate;

if said first treated diameter is determined not to be sufficient to establish said desired blood flow rate, inflating said secondary chambers to achieve said second preselected diameter.

24. A method in accordance with claim 23 wherein said shaft further comprises a third lumen; and said catheter further comprises: a tertiary balloon comprising an array formed of a plurality of radially disposed inflatable tertiary chambers disposed cylindrically about said secondary balloon, wherein each of said tertiary chambers is defined by at least an inner wall and an outer wall, said secondary chamber outer walls providing said inner walls for said tertiary chambers; and means to inflate each of said tertiary chambers to a third preselected diameter, said means including a plurality of channels, each channel being in fluid communication with one of said tertiary chambers and with said third lumen; and further comprising the steps of:

- examining said constricted portion to determine whether said second treated diameter is sufficient to establish said desired blood flow rate;
- if said second treated diameter is determined not to be sufficient to establish said desired blood flow rate, inflating said tertiary chambers to said third preselected diameter.

25. A method for administering treatment to widen a constricted portion of a bodily conduit to establish a desired blood flow rate through said constricted portion, said method comprising the steps of:

- inserting a catheter having an inflatable balloon into said bodily conduit to position said balloon within said constricted portion, said catheter comprising a shaft comprising at least first and second lumens for delivery of fluid inflation media; a primary balloon having a generally cylindrical wall concentric with said shaft and defining a primary chamber, said primary chamber being in fluid communication with said first lumen for inflation of said primary balloon to a first preselected diameter; a secondary balloon comprising an array formed of a plurality of radially disposed inflatable secondary chambers disposed cylindrically about said primary balloon, wherein each of said secondary chambers is defined by at least an inner wall and an outer wall, said primary balloon wall providing said inner wall for each of said secondary chambers; means to inflate at least one of said secondary chambers to achieve a second preselected diameter greater than said first preselected diameter, said means including at least one channel in fluid communication with said at least one secondary chamber and with said second lumen;
- inflating said primary balloon to said first preselected diameter to engage said constricted portion and to widen said constricted portion to a first treated diameter;
- examining said constricted portion to determine whether said first treated diameter is sufficient to establish said desired blood flow rate;
- if said first treated diameter is determined not to be sufficient to establish said desired blood flow rate, inflating said at least one secondary chamber to achieve said second preselected diameter.

26. A method in accordance with claim 25 wherein said shaft further comprises at least a third lumen for delivery of fluid inflation media; said array of secondary chambers includes at least a first set and a second set of said secondary chambers, each set including at least one secondary chamber; and said inflation means includes a plurality of channels, each channel being in fluid communication with one of said secondary chambers, each of the secondary chambers of said first set being in fluid communication through its associated channel with said second lumen, and each of the secondary chambers of said second set being in fluid communication through its associated channel with said third lumen; wherein said step of inflating said at least one secondary chamber comprises inflating said first set of said secondary chambers to achieve said second preselected diameter; and further comprising the steps of

- reexamining said constricted portion to determine whether said second treated diameter is sufficient to establish said desired blood flow rate;
- if said second treated diameter is determined not to be sufficient to establish said desired blood flow rate, inflating said second set of said secondary chambers to achieve a third preselected diameter.

27. A method in accordance with claim 26 wherein said fluid communication between said first set of secondary chambers and associated channels and said second lumen is provided by a first manifold formed between said channels and said second lumen, and said fluid communication between said second set of secondary chambers and associated channels and said third lumen is provided by a second manifold formed between said channels and said third lumen.

28. A method in accordance with claim 25 wherein said shaft further comprises a third lumen; and said catheter further comprises: a tertiary balloon comprising an array formed of a plurality of radially disposed inflatable tertiary chambers disposed cylindrically about said secondary balloon, wherein each of said tertiary chambers is defined by at least an inner wall and an outer wall, said secondary chamber outer walls providing said inner walls for said tertiary chambers; and means to inflate at least one of said tertiary chambers to achieve a third preselected diameter, said means including at least one channel in fluid communication with said at least one tertiary chamber and with said third lumen; and further comprising the steps of:

- examining said constricted portion to determine whether said second treated diameter is sufficient to establish said desired blood flow rate;
- if said second treated diameter is determined not to be sufficient to establish said desired blood flow rate, inflating said at least one tertiary chamber to achieve said third preselected diameter.

* * * * *